United States Patent [19]

Gribble et al.

[11] Patent Number: 4,728,648
[45] Date of Patent: * Mar. 1, 1988

[54] HISTAMINE ANTAGONIST TRIADIAZOLE DERIVATIVES, COMPOSITIONS, AND METHOD OF USE THEREFOR

[75] Inventors: Andrew D. Gribble, Woolmer Green; Robert J. Ife, Stevenage, both of England

[73] Assignee: Smith Kline & French Laboratories Limited, Welwyn Garden City, Great Britain

[*] Notice: The portion of the term of this patent subsequent to Jul. 30, 2002 has been disclaimed.

[21] Appl. No.: 826,158

[22] Filed: Feb. 4, 1986

[30] Foreign Application Priority Data

Feb. 9, 1985 [GB] United Kingdom ............... 8503391
Apr. 2, 1985 [GB] United Kingdom ............... 8508606

[51] Int. Cl.[4] ............... A61K 31/38; A61K 31/425; A61K 31/44; A61K 31/495

[52] U.S. Cl. .................... 514/252; 514/255; 514/256; 514/333; 514/342; 544/238; 544/331; 544/405; 546/256; 546/271; 546/277; 546/278

[58] Field of Search ............... 544/238, 331, 333, 405; 546/277, 278, 256, 271; 514/79, 91, 97, 252, 255, 256, 333, 342

[56] References Cited

U.S. PATENT DOCUMENTS

| | | | |
|---|---|---|---|
| 4,374,248 | 2/1983 | Crenshaw et al. | 514/275 |
| 4,394,508 | 7/1983 | Crenshaw et al. | 514/275 |
| 4,532,246 | 7/1985 | Ife | 514/275 |
| 4,532,252 | 7/1985 | Sach | 514/275 |

*Primary Examiner*—Alan L. Rotman
*Assistant Examiner*—J. G. Mullins
*Attorney, Agent, or Firm*—Linda E. Hall; Janice E. Williams; Alan D. Lourie

[57] ABSTRACT

New 3,4-diamino-1,2,5-thiadiazole oxide derivatives which are histamine $H_1$-antagonists. A specific compound of this invention is 3-[3-[N-(4-fluorobenzyl)-N-pyrid-2-yl-amino]propylamino]-4-[pyrimidin-4-yl-methylamino]-1,2,5-thiadiazole-1-oxide.

22 Claims, No Drawings

HISTAMINE ANTAGONIST TRIADIAZOLE DERIVATIVES, COMPOSITIONS, AND METHOD OF USE THEREFOR

This invention relates to certain pyridine derivatives, pharmaceutical compositions containing them and a method of blocking histamine $H_1$-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine.

According to the present invention there is provided compounds of formula (1):

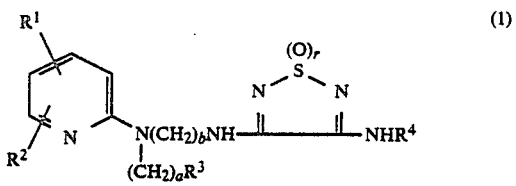

and pharmaceutically acceptable salts thereof, where $R^1$ and $R^2$ are the same or different and are hydrogen, $C_{1-6}$ alkyl, $C_{1-6}$ alkoxy or halogen;

$R^3$ is optionally substituted phenyl or optionally substituted pyridyl, where the optional substituents are one or more $C_{1-6}$ alkyl, $C_{1-6}$ alkoxy, or hydroxy groups or halogen atoms; or furanyl or thienyl optionally substituted by a $C_{1-6}$ alkyl group;

a is from 1 to 6;

b is from 2 to 4;

$R^4$ is $CH_2R^5$ where $R^5$ is phenyl substituted by sulphonamido or a carboxyl group or an ester thereof, pyridyl substituted with a carboxyl group or an ester thereof and optionally further substituted with a $C_{1-6}$ alkyl group, N-oxo-pyridyl optionally substituted with a $C_{1-6}$ alkyl group, or an imidazolyl, pyridazinyl, pyrimidinyl, pyrazinyl or benzimidazolyl group; and r is 1 or 2.

The compounds of this invention are histamine $H_1$-antagonists and are useful for the treatment of diseases for example bronchial asthma, rhinitis, hayfever and allergic eczema whose symptoms are mediated through the action of histamine at $H_1$-receptors.

Examples of halogens for $R^1$ and $R^2$ are fluorine, chlorine, bromine and iodine.

Examples of $C_{1-6}$ alkyl groups for $R^1$, $R^2$ and the $C_{1-6}$ alkyl substituent in $R^3$ and $R^5$ are methyl, ethyl, n-propyl, iso-propyl, n-butyl and t-butyl.

Examples of $C_{1-6}$ alkoxy groups for $R^1$, $R^2$ and the $C_{1-6}$ alkoxy substituents in $R^3$ are methoxy, ethoxy, n-propoxy and n-butoxy.

Examples of esters of carboxyl derivatives are $C_{1-6}$ alkyl esters.

Preferably $R^1$ and $R^2$ are both hydrogen.

By way of example, a can be 1, 2 or 3. Preferably it is 1.

By way of example, b can be 2, 3 or 4. Preferably it is 3.

Examples of substituted phenyl groups for $R^3$ are 2-methylphenyl, 2-methoxyphenyl, 2-chlorophenyl, 2-fluorophenyl, 3-methylphenyl, 3-methoxyphenyl, 3-chlorophenyl, 3-fluorophenyl, 4-methylphenyl, 4-methoxyphenyl, 4-chlorophenyl and 4-fluorophenyl.

Where $R^3$ is an optionally substituted pyridyl group it can be pyrid-2-yl, pyrid-3-yl, and pyrid-4-yl groups.

Where $R^3$ is an optionally substituted furanyl group it can be furan-2-yl and furan-3-yl.

Where $R^3$ is an optionally substituted thienyl group it can be thien-2-yl and thien-3-yl.

In particular, a is 1 and $R^3$ is phenyl, 2-chlorophenyl, 2-fluorophenyl, 3-chlorophenyl, 3-fluorophenyl, 4-chlorophenyl, 4-fluorophenyl, thien-2-yl, thien-3-yl, furan-2-yl, pyrid-2-yl, pyrid-3-yl or pyrid-4-yl.

Preferably $R^3$ is phenyl, 4-fluorophenyl, thien-2-yl, thien-3-yl, furan-2-yl or furan-3-yl.

Where $R^5$ is phenyl or pyridyl substituted with a carboxyl group, the compound can exist in a zwitterionic form.

Where $R^5$ is substituted phenyl, preferably the substituent is in a position para to the point of attachment of the methylene group.

Where $R^5$ is a substituted pyridyl group, preferably it is a 6-carboxy pyrid-3-yl group.

Where $R^5$ is N-oxo-pyridyl, the methylene group is attached in particular at position 4 of the pyridyl group.

Examples of particular values for $R^5$ are 4-carboxyphenyl, 4-sulphonamidophenyl, 6-carboxypyrid-3-yl, 2-methyl-N-oxo-pyrid-4-yl, N-oxo-pyrid-4-yl, imidazol-2-yl, imidazol-4-yl, pyridazin-3-yl, pyridazin-4-yl, pyrimidin-2-yl, pyrimidin-4-yl, pyrazin-2-yl and benzimidazol-2-yl.

Preferably $R^5$ is 4-sulphonamidophenyl, imidazol-4-yl, imidazol-2-yl or pyrimidin-4-yl.

Preferably r is 1.

Particular compounds within the scope of this invention are:

3-[3-(N-thien-2-ylmethyl-N-pyrid-2-ylamino)-propylamino]-4-(4-sulphonamidobenzylamino)-1,2,5-thiadiazole-1-oxide;

3-[3-(N-4-fluorobenzyl-N-pyrid-2-ylamino)-propylamino]-4-benzimidazol-2-ylmethylamino-1,2,5-thiadiazole-1-oxide;

3-[3-(N-4-fluorobenzyl)-N-pyrid-2-ylamino)-propylamino]-4-(4-sulphonamidobenzylamino)-1,2,5-thiadiazole-1-oxide;

3-[3-(N-4-fluorobenzyl))-N-pyrid-2-ylamino)-propylamino]-4-imidazol-4-ylmethylamino-1,2,5-thiadiazole-1-oxide;

3-[3-[N-(4-fluorobenzyl)-N-pyrid-2-ylamino]-propylamino-4-(pyrid-2-ylamino)propylamino]-4-(4-carboxybenzylamino)-1,2,5-thiadiazole-1-oxide;

3-[3-[N-(4-fluorobenzyl)-N-pyrid-2-ylamino]-propylamino]-4-(pyrazin-2-ylmethylamino)-1,2,5-thiadiazole-1-oxide;

3-[3-[N-(4-fluorobenzyl)-N-pyrid-2-ylamino]-propylamino]-4-(pyridazin-3-ylmethylamino)-1,2,5-thiadiazole-1-oxide;

3-[3-[N-(4-fluorobenzyl)-N-pyrid-2-ylamino]-propylamino]-4-imidazol-2-ylmethylamino-1,2,5-thiadiazole-1-oxide;

3-[3-[N-(4-fluorobenzyl)-N-pyrid-2-ylamino]-propylamino]-4-(N-oxo-pyrid-4-ylmethylamino)-1,2,5-thiadiazole-1-oxide;

3-[3-[N-(4-fluorobenzyl)-N-pyrid-2-ylamino]-propylamino]-4-pyrimidin-4-ylmethylamino-1,2,5-thiadiazole-1-oxide;

3-[3-[N-(4-fluorobenzyl)-N-pyrid-2-ylamino]-
propylamino]-4-pyrimidin-2-ylmethylamino-1,2,5-
thiadiazole-1-oxide;

3-[3-[N-(thien-2-ylmethyl)-N-pyrid-2-ylamino]-
propylamino]-4-benzimidazol-2-ylmethylamino-
1,2,5-thiadiazole-1-oxide;

3-[3-[N-benzyl-N-pyrid-2-ylamino]propylamino]-4-benzimidazol -2-ylmethylamino-1,2,5-thiadiazole-1-oxide;

3-[3-(N-furan-2-ylmethyl-N-pyrid-2-ylamino)-
propylamino-2-benzimidazol-2-ylmethylamino-1,2,5-
thiadiazole-1-oxide;

and their pharmaceutically acceptable salts.

Compounds of formula (1) also form pharmaceutically acceptable salts with pharmaceutically acceptable acid addition salt-forming acids and with pharmaceutically acceptable salt-forming bases when $R^5$ is phenyl or pyridyl substituted with carboxyl. Accordingly, in this specification the term "pharmaceutically acceptable salts" means salts with bases or acid addition salts as the context requires.

Examples of pharmaceutically acceptable acid addition salt-forming acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Examples of suitable salts of the carboxyl group include alkali metal salts, especially the sodium and potassium salts.

Compounds of formula (1) can be prepared by reacting an amine of formula (2):

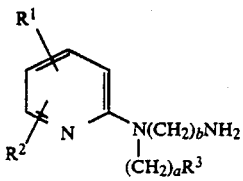

where $R^1$, $R^2$, $R^3$, a and b are as defined with reference to formula (1), with a compound of formula (3):

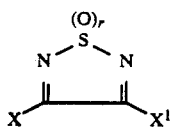

where X is a group displaceable with an amine and $X^1$ is a group displaceable with an amine or a group of formula $NHR^4$ where $R^4$ is as previously defined, and where $X^1$ is a group displaceable with an amine, thereafter reacting with an amine of formula (4):

where $R^4$ is as defined with reference to formula (1).

Examples of leaving groups displaceable by amines are where X and $X^1$ are QS—, QSO—, $QSO_2$—, or QO— (Q being $C_{1-6}$ alkyl, aryl or aralkyl), halogen, particularly chlorine and bromine, and nitroamino. Preferably the groups X and $X^1$ are QO— where Q is methyl.

The conditions under which the reaction is carried out depends upon the nature of the reagents. The reaction is carried out at moderate to low temperature e.g. from 0° C. to room temperature. The choice of solvent is affected by the solubility characteristics of the reagents. Preferably the solvent is pyridine, a picoline or mixture of picolines, a $C_{1-6}$ alkanol, preferably methanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide or sulpholane.

Where $R^5$ in the compound of formula (1) is phenyl substituted with a carboxyl group, the carboxyl group can be converted into a pharmaceutically acceptable salt by standard methods for example by reacting the compound in solution with a solution of a base.

Pharmaceutically acceptable acid addition salts of compounds of formula (1) can be prepared by standard methods, for example by reacting a solution of the compound of formula (1) with a solution of the acid.

Compounds of formula (2) can be prepared by reacting a compound of formula (5):

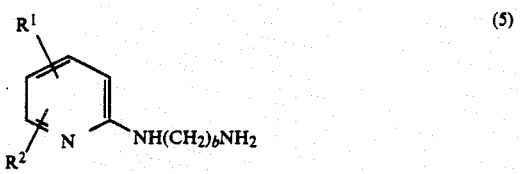

where $R^1$ and $R^2$ and b are as defined with reference to formula (1) or a derivative thereof where the primary amino group is protected, with a compound of formula (6):

$$R^3(CH_2)_aX^2 \qquad (6)$$

where $R^3$ and a are as defined with reference to formula (1) (provided that any hydroxy groups in $R^3$ are protected) and $X^2$ is halogen, in the presence of a strong base and thereafter removing any protecting groups.

Compounds of formula (5) can be prepared in turn by reacting a compound of formula (7):

where $R^1$ and $R^2$ are as defined with reference to formula (1) and $X^2$ is halogen with an amine of formula (8):

$$NH_2(CH_2)_bNH_2 \qquad (8)$$

Compounds of formula (5) can also be prepared by reacting a compound of formula (9):

where $R^1$, $R^2$, $R^3$ and a are as defined with reference to formula (1) (provided that any hydroxy groups in $R^3$ are protected) with a compound of formula (10):

$$X^2(CH_2)_bR^6 \qquad (10)$$

where b is as defined with reference to formula (1), $X^2$ is halogen and $R^6$ is a protected amino group, in the presence of a strong base and thereafter removing any protecting groups.

Examples of hydroxy protecting groups are $C_{1-6}$ alkyl, for example methyl, and $C_{1-6}$ alkanoyl, for example formyl or acetyl.

These protecting groups can be removed by standard methods, in particular under basic conditions.

Examples of protected amino groups for $R^6$ include phthalimido. In formulae (6), (7) and (10) $X^2$ can be chlorine, bromine or iodine.

Examples of strong bases are alkali metal hydrides, particularly sodium hydride. The reaction is carried out in the presence of a polar solvent for example dimethylsulphoxide.

The protected amino group can be converted into amino by standard methods, for example when it is phthalimido by reaction with hydrazine.

The use of protecting groups is discussed in T. W. Greene, Protective Groups in Organic Synthesis, 1981, John Wiley & Sons, IBSN 0-471-05764-9.

Compounds of formulae (3) are known or can be made by known methods as described in for example British Patent Application No. 2067987A.

Compounds of formulae (6) to (10) are known or can be made by known methods.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of the Examples have $pA_2$ values greater than 7.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Topical formulations for administration to the eye include solutions and ointments. Solutions for administration to the eye comprise the active compound and a sterile aqueous carrier for example an isotonic buffer particularly a buffered solution of boric acid, sodium chloride or sodium borate. The buffer can be a conventional phosphate buffer which maintains the pH of the solution in a physiological pH range. An example of such a buffer is Sorensen's buffer. For an ointment the carrier can be petrolatum.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever, rhinitis or allergic eczema.

Each dosage unit for oral administration contains preferably from 5 to 200 mg of a compound of formula (1) or a pharmaceutically acceptable salt thereof calculated as the free base.

The invention also includes a method of blocking histamine $H_1$-receptors which comprises administering to a subject an effective amount to block said receptors of a compound of formula (1).

The compounds of the invention will normally be administered to a subject for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

2-[N-(3-Aminopropyl)-N-thien-2-ylmethylamino]-pyridine (1.5 g) in methanol (15 ml) was added dropwise to a stirred solution of 3,4-dimethoxy-1,2,5-thiadiazole-1-oxide (0.98 g) in methanol (70 ml) at 5° C. After 2 hr. a solution of 4-aminomethylbenzenesulphonamide (from 1.78 g of its hydrochloride salt and 0.18 g sodium) in methanol (20 ml) was added and the mixture was allowed to stand for 2.5 days at room temperature. The solvent was evaporated and the residue chromatographed (silica gel, chloroform/methanol 20:1) to give, after crystallisation from ethanol, 3-[3-(N-thien-2-ylmethyl-N-pyrid-2-ylamino)propylamino]-4-(4-sulphonamidobenzylamino)-1,2,5-thiadiazole-1-oxide (1.73 g; 54%) m.p. 175°-176° C. (decomp.).

$C_{22}H_{25}N_7O_3S_3$:

Found: C 49.82, H 4.80, N 18.64. Requires: C 49.70, H 4.74, N 18.44.

EXAMPLE 2

2-[N-(3-Aminopropyl)-N-thien-2-ylmethylamino]-pyridine (1.5 g) in methanol (30 ml) was added dropwise to a stirred solution of 3,4-dimethoxy-1,2,5-thiadiazole-1-oxide (0.98 g) in methanol (70 ml) at 5°-10° C. over 0.5 hr. After 2 hr. a solution of 2-aminomethylbenzimidazole (from 1.7 g of its dihydrochloride salt and 0.34 g of sodium) in methanol (20 ml) was added and after a further 3 hr. at 5°-10° C. The mixture was allowed to stand for 3 days at room temperature. The solvent was evaporated and the residue chromatographed (silica gel, chloroform/methanol 20:1) to give, after crystallisation from ethanol, 3-[3-(N-thien-2-ylmethyl-N-pyrid-2-ylamino) propylamino]-4-benzimidazol-2-ylmethylamino-1,2,5-thiadiazole-1-oxide (0.86 g; 31%) m.p. 211.5°-212° C. (decomp.).

$C_{23}H_{24}N_8OS_2$:

Found: C 56.36, H 4.95, N 22.93. Requires: C 56.08, H 4.91, N 22.75.

EXAMPLE 3

2-[N-(3-Aminopropyl)-N-(4-fluorobenzyl)amino]-pyridine (1.0 g) in methanol (10 ml) was added dropwise to a stirred suspension of 3,4-dimethoxy-1,2,5-thiadiazole-1-oxide (0.63 g) in methanol (40 ml) at 0°-5° C. After 2.5 hr. at 5°-10° C., a solution of 4-aminomethylbenzenesulphonamide [prepared from the hydrochloride salt (1.29 g) and sodium (0.13 g)]in methanol (15 ml) was added. The mixture was allowed to stand overnight and then evaporated to dryness. The residue was chromatographed (silica gel, dichloromethane/methanol, 20:1) to give, after crystallisation from ethanol/water, 3-[3-[N-(4-fluorobenzyl)-N-pyrid-2-ylamino]propylamino]-4-(4-sulphonamidobenzylamino)-1,2,5-thiadiazole-1-oxide (1.25 g; 60%) m.p. 184°-187° C.

$C_{24}H_{26}FN_7O_3S_2$:

Found: C 53.15, H 4.96, N 18.00, S 11.63. Requires: C 53.02, H 4.82, N 18.04, S 11.80.

EXAMPLE 4

2-[N-(3-Aminopropyl)-N-(4-fluorobenzyl)amino]-pyridine (1.68 g) in methanol (15 ml) was added dropwise to a stirred suspension of 3,4-dimethoxy-1,2,5-thiadiazole-1-oxide (1.05 g) in methanol (35 ml) at 0° C. After 1 hr. at room temperature, a mixture of 4-aminomethylimidazole dihydrochloride and triethylamine (1.33 g) was added and the mixture was allowed to stand overnight. The solvent was evaporated from the mixture and the residue was chromatographed (silica gel, chloroform/methanol 10:1). The solvent was evaporated from the fractions containing the required product and the residue treated with maleic acid in ethanol to give, after crystallisation from ethanol/ether, 3-[3-[N-(4-fluorobenzyl)-N-pyrid-2-ylamino]propylamino]-4-(imidazol-4-yl-methylamino)-1,2,5-thiadiazole-1-oxide dimaleate (0.59 g; 13%) m.p. indeterminate.

$C_{21}H_{23}N_8FOS.2C_4H_4O_4$:

Found: C 50.51, H 4.63, N 16.11, S 4.58. Requires: C 50.72, H 4.55, N 16.32, S 4.67.

EXAMPLE 5

A solution of 4-carboxybenzylamine (0.76 g), 3,4-dimethoxy-1,2,5-thiadiazole-1-oxide (0.81 g) and triethylamine (0.52 g) in methanol (350 ml) and water (50 ml) was stirred at room temperature for 1 hr. To this was added a solution of 2-[N-(3-aminopropyl)-N-(4-fluorobenzyl)amino]pyridine (1.3 g) in methanol (10 ml). The mixture was allowed to stand overnight and then evaporated to dryness. The residue was chromatographed (silica gel, chloroform/methanol 9:1) to give, after washing with n-propanol and trituration with ether, 3-[3-[N-(4-fluorobenzyl)-N-pyrid-2-ylamino]propylamino]-4-(4-carboxybenzylamino)-1,2,5-thiadiazole-1-oxide (0.14 g; 6%) m.p. indeterminate.

EXAMPLE 6

2-[N-(3-Aminopropyl)-N-(4-fluorobenzyl)amino]-pyridine (1.6 g) in methanol (20 ml) was added dropwise to a stirred solution of 3,4-dimethoxy-1,2,5-thiadiazole-1-oxide (1.0 g) in methanol (40 ml) at 0°-5°

C. After 2 hr. at room temperature, a solution of 4-aminomethylpyrimidine (0.67 g) in methanol (10 ml) was added at 0°–5° C. with stirring. The mixture was allowed to stand overnight and evaporated to dryness. The residue was chromatographed (silica gel, 3% CH$_3$OH/CHCl$_3$) to give, after crystallisation from ethyl acetate, 3-[3-[N-(4-fluorobenzyl)-N-pyrid-2-ylamino]propylamino]-4-[pyrimidin-4-ylmethylamino]-1,2,5-thiadiazole-1-oxide (0.34g, 12%), m.p. 134°–135° C.

C$_{22}$H$_{23}$FN$_8$OS:
Found: C 56.52, H 5.08, N 23.84, S 6.57. Requires: C 56.64, H 4.97, N 24.02, S 6.87.

EXAMPLE 7

(a) To 4-aminomethylpyridine (15 g) cooled to 0° C. was added, with stirring, acetic anhydride (15 ml). After 30 min., the dark viscous oil was taken up in chloroform and extracted with 5% sodium bicarbonate solution (3x). The pH of the aqueous extracts was adjusted to ca. 8, saturated with sodium chloride and extracted with chloroform. Concentration afforded 4-pyridylmethylacetamide (9.60 g, 50%) as a yellow solid. To the latter (6.9 g) in dichloromethane (100 ml) was added m-chloroperbenzoic acid (10.2 g) in dichloromethane (50 ml) at 0° C. over 0.5 hr. The mixture was left overnight at room temperature and concentrated. The residue was chromatographed (silica, 10% rising to 25% CH$_3$OH/CHCl$_3$) to give pyrid-1-oxo-4-ylmethylacetamide (7.17 g, 93%) as an off-white solid. The latter (5.8 g) was heated under reflux with 95% ethanol (20 ml) and concentrated hydrochloric acid (20 ml) for 1.5 hr. Cooling afforded 4-aminomethylpyridine-1-oxide dihydrochloride (3.85 g, 52%) as a precipitate; m.p. (from ethanol) 176°–178° C.

(b) Substituting 4-aminomethylpyridine-1-oxide for 4-aminomethylbenzenesulphonamide in the method of Example 3 gave 3-[3-[N-(4-fluorobenzyl)-N-pyrid-2-ylamino]propylamino]-4-(1-oxopyrid-4-ylmethylamino)-1,2,5-thiadiazole-1-oxide, m.p. 202° C. (decomp.).

Found: C 57.11, H 5.09, N 19.96, S 6.58. C$_{23}$H$_{24}$FN$_7$O$_2$S: C 57.37; H 5.02, N 20.36, S 6.66.

EXAMPLES 8 to 10

Substituting 2-aminomethylimidazole, 2-aminomethylbenzimidazole and 2-aminomethylpyrazine for 4-aminomethylbenzenesulphonamide in the method of Example 3 gave, respectively:

EXAMPLE 8

3-[3-[N-(4-fluorobenzyl)-N-pyrid-2-ylamino]-propylamino]-4-(imidazol-2-ylmethylamino)-1,2,5-thiadiazole-1-oxide; m.p. 196°–197° C.
Found: C 55.53, H 5.14, N 24.47, S 7.33. C$_{21}$H$_{23}$FN$_8$OS: C 55.49, H 5.10, N 24.65, S 7.05.

EXAMPLE 9

3-[3-[N-(4-fluorobenzyl)-N-pyrid-2-ylamino]-propylamino]-4-(benzimidazol-2-ylmethylamino)-1,2,5-thiadiazole-1-oxide; m.p. 208°–209° C.
Found: C 59.37, H 5.02, N 21.96, S 6.41. C$_{25}$H$_{25}$FN$_8$OS: C 59.51, H 4.99, N 22.08, S 6.35.

EXAMPLE 10

3-[3-[N-(4-fluorobenzyl)-N-pyrid-2-ylamino]-propylamino]-4-(pyrazin-2-ylmethylamino)-1,2,5-thiadiazole-1-oxide; m.p. 131°–133° C.

Found: C 56.53, H 5.03, N 23.77, S 7.10. C$_{22}$H$_{23}$FN$_8$OS: C 56.64, H 4.97, N 24.02, S 6.87.

EXAMPLE 11

(a) Pyridazine-3-carboxaldehyde oxime was prepared from 3-methylpyridazine using the general method of Forman (J. Org. Chem., 1964, 29, 3323). This (0.6 g) in methanol (75 ml) was hydrogenated in a Parr vessel at 40 p.s.i. using 10% palladium on charcoal (0.05 g) for 3 hr. Filtration and evaporation gave 3-aminomethylpyridazine (0.52 g, 99%) as an oil which was used without further purification.

(b) Substituting 3-aminomethylpyridazine for 4-aminomethylbenzenesulphonamide in the method of Example 3 gave 3-[3-[N-(4-fluorobenzyl)-N-pyrid-2-ylamino]propylamino]-4-(pyridazin-3-ylmethylamino)-1,2,5-thiadiazole-1-oxide, m.p. indeterminate.

Found: C 54.77, H 4.85, N 22.86, S 6.94. C$_{22}$H$_{23}$FN$_8$OS. 0.65H$_2$O.0.05CHCl$_3$ requires: C 54.72, H 5.07, N 23.15, S 6.63.

EXAMPLES 12 and 13

Substituting 2-[N-(3-aminopropyl)-N-benzylamino]-pyridine and 2-[N-(3-aminopropyl)-N-furan-2-ylmethylamino]pyridine for 2-[N-(3-aminopropyl-N-thien-2-ylmethylamino]pyridine in the method of Example 2 gave respectively:

EXAMPLE 12

3-[3-(N-benzyl-N-pyrid-2-ylamino)propylamino]-4-(benzimidazol-2-ylmethylamino)-1,2,5-thiadiazole-1-oxide. 0.3H$_2$O; m.p. 210°–211° C.
Found: C 61.09, H 5.38, N 22.68, S 6.66. C$_{25}$H$_{26}$N$_8$OS.0.3H$_2$O: C 61.03, H 5.44, N 22.77, S 6.52.

EXAMPLE 13

3-[3-(N-furan-2-ylmethyl-N-pyrid-2-ylamino)-propylamino]-4-benzimidazol-2-ylmethylamino)-1,2,5-thiadiazole-1-oxide; m.p. 208°–209° C.
Found: C 58.03, H 4.96, N 23.29, S 6.72. C$_{23}$H$_{24}$N$_8$O$_2$S: C 57.97, H 5.08, N 23.51, S 6.73.

EXAMPLE 14

A pharmaceutical composition for oral administration is prepared containing

| | | % by weight |
|---|---|---|
| A | 3-[3-[N—(4-fluorobenzyl)-N—pyrid-2-ylamino]propylamino]-4-[pyrimidin-4-ylmethylamino]-1,2,5-thiadiazole-1-oxide | 55 |
| | Dibasic calcium phosphate dihydrate | 20 |
| | Approved coloring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 15

A pharmaceutical composition for injectable administration is prepared by forming a solution of 3-[3-[N-(4-fluorobenzyl)-N-pyrid-2-ylamino]propylamino]-4-[pyrimidin-4-ylmethylamino]-1,2,5-thiadiazole-1-oxide in sterile water to give a 1 to 5% w/w solution. The solution is clarified by filtration and filled into vials which are sealed and sterilised. A suitable vial contains 2 ml of the solution.

What is claimed is:

1. A compound of formula (1):

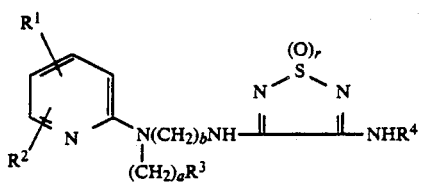

or a pharmaceutically acceptable salt thereof, where
$R^1$ and $R^2$ are the same or different and are hydrogen, $C_{1-6}$ alkyl, $C_{1-6}$ alkoxy or halogen;
$R^3$ is optionally substituted phenyl or optionally substituted pyridyl, where the optional substituents are one or more $C_{1-6}$ alkyl, $C_{1-6}$ alkoxy, or hydroxy groups or halogen atoms; or furanyl or thienyl optionally substituted by a $C_{1-6}$ alkyl group;
a is from 1 to 6;
b is from 2 to 4;
$R^4$ is $CH_2R^5$ where $R^5$ is phenyl substituted by sulphonamido or a carboxyl group or an ester thereof, pyridyl substituted with a carboxyl group or an ester thereof and optionally further substituted with a $C_{1-6}$ alkyl group, N-oxo-pyridyl optionally substituted with a $C_{1-6}$ alkyl group, or an imidazolyl, pyridazinyl, pyrimidinyl, pyrazinyl or benzimidazolyl group; and
r is 1 or 2.

2. A compound as claimed in claim 1 where $R^1$ and $R^2$ are both hydrogen.

3. A compound as claimed in claim 1 or claim 2 where a is 1.

4. A compound as claimed in claim 1 where b is 3.

5. A compound as claimed in claim 1 where $R^3$ is phenyl, 4-fluorophenyl, thien-2-yl, thien-3-yl, furan-2-yl or furan-3-yl.

6. A compound as claimed in claim 1 where $R^5$ is 4-sulphonamidophenyl, imidazol-4-yl, imidazol-2-yl or pyrimidin-4-yl.

7. A compound as claimed in claim 1 where r is 1.

8. A compound of claim 1, said compound being 3-[3-(N-thien-2-ylmethyl-N-pyrid-2-ylamino)-propylamino]-4-(4-sulphonamidobenzylamino)-1,2,5-thiadiazole-1-oxide or a pharmaceutically acceptable acid addition salt thereof.

9. A compound of claim 1, said compound being 3-[3-(N-4-fluorobenzyl-N-pyrid-2-ylamino)-propylamino]-4-benzimidazol-2-ylmethylamino-1,2,5-thiadiazole-1-oxide or a pharmaceutically acceptable acid addition salt thereof.

10. A compound of claim 1, said compound being 3-[3-(N-4-fluorobenzyl)-N-pyrid-2-ylamino)-propylamino]-4-(4-sulphonamidobenzylamino)-1,2,5-thiadiazole-1-oxide or a pharmaceutically acceptable acid addition salt thereof.

11. A compound of claim 1, said compound being 3-[3-(N-4-fluorobenzyl)-N-pyrid-2-ylamino)-propylamino]-4-imidazol-4-ylmethylamino-1,2,5-thiadiazole-1-oxide or a pharmaceutically acceptable acid addition salt thereof.

12. A compound of claim 1, said compound being 3-[3-[N-(4-fluorobenzyl)-N-pyrid-2-ylamino]-propylamino-4-(pyrid-2-ylamino)propylamino]-4-(4-carboxybenzylamino)-1,2,5-thiadiazole-1-oxide or a pharmaceutically acceptable acid addition salt thereof.

13. A compound of claim 1, said compound being 3-[3-[N-(4-fluorobenzyl)-N-pyrid-2-ylamino]-propylamino]-4-(pyrazin-2-ylmethylamino)-1,2,5-thiadiazole-1-oxide or a pharmaceutically acceptable acid addition salt thereof.

14. A compound of claim 1, said compound being 3-[3-[N-(4-fluorobenzyl)-N-pyrid-2-ylamino]-propylamino]-4-(pyridazin-3-ylmethylamino)-1,2,5-thiadiazole-1-oxide or a pharmaceutically acceptable acid addition salt thereof.

15. A compound of claim 1, said compound being 3-[3-[N-(4-fluorobenzyl)-N-pyrid-2-ylamino]-propylamino]-4-imidazol-2-ylmethylamino-1,2,5-thiadiazole-1-oxide or a pharmaceutically acceptable acid addition salt thereof.

16. A compound of claim 1, said compound being 3-[3-[N-(4-fluorobenzyl)-N-pyrid-2-ylamino]-propylamino]-4-(N-oxo-pyrid-4-ylmethylamino)-1,2,5-thiadiazole-1-oxide or a pharmaceutically acceptable acid addition salt thereof.

17. A compound of claim 1, said compound being 3-[3-[N-(4-fluorobenzyl)-N-pyrid-2-ylamino]-propylamino]-4-pyrimidin-4-ylmethylamino-1,2,5-thiadiazole-1-oxide or a pharmaceutically acceptable acid addition salt thereof.

18. A compound of claim 1, said compound being 3-[3-[N-(thien-2-ylmethyl)-N-pyrid-2-ylamino]-propylamino]-4-benzimidazol-2-ylmethylamino-1,2,5-thiadiazole-1-oxide or a pharmaceutically acceptable acid addition salt thereof.

19. A compound of claim 1, said compound being 3-[3-[N-benzyl-N-pyrid-2-ylamino]propylamino]-4-benzimidazol-2-ylmethylamino-1,2,5-thiadiazole-1-oxide or a pharmaceutically acceptable acid addition salt thereof.

20. A compound of claim 1, said compound being 3-[3-(N-furan-2-ylmethyl-N-pyrid-2-ylamino)-propylamino-2-benzimidazol-2-ylmethylamino-1,2,5-thiadiazole-1-oxide or a pharmaceutically acceptable acid addition salt thereof.

21. A pharmaceutical composition for blocking histamine $H_1$-receptors which comprises administering to a subject an effective amount to block said receptors of a compound according to claim 1.

22. A method of blocking histamine $H_1$-receptors which comprises administering to a subject an effective amount to block said receptors of a compound according to claim 1.

* * * * *